US005213789A

United States Patent [19]

Degenhardt et al.

[11] Patent Number: 5,213,789

[45] Date of Patent: May 25, 1993

[54] USE OF A CARBOXY-CONTAINING COPOLYMER TO INHIBIT PLAQUE FORMATION WITHOUT TOOTH STAINING

[75] Inventors: Charles R. Degenhardt; Barbara A. Kozikowski, both of Cincinnati, Ohio

[73] Assignee: The Procter & Gamble Company, Cincinnati, Ohio

[21] Appl. No.: 815,569

[22] Filed: Dec. 26, 1991

Related U.S. Application Data

[63] Continuation of Ser. No. 561,832, Aug. 2, 1990, abandoned.

[51] Int. Cl.[5] .......................... A61K 7/16; A61K 7/18

[52] U.S. Cl. .......................................... 424/52; 424/49

[58] Field of Search ..................................... 424/49–58

[56] References Cited

U.S. PATENT DOCUMENTS

| | | | |
|---|---|---|---|
| 3,429,963 | 2/1969 | Shedlovsky | 424/56 |
| 4,089,830 | 5/1978 | Tezuka et al. | 260/29.6 H |
| 4,118,473 | 10/1978 | Gaffar et al. | 424/54 |
| 4,118,474 | 10/1978 | Gaffar et al. | 424/54 |
| 4,138,477 | 2/1979 | Gaffar | 424/52 |
| 4,224,309 | 9/1980 | Gaffar et al. | 424/54 |
| 4,362,713 | 12/1982 | Buck | 424/54 |
| 4,375,461 | 3/1983 | Gander et al. | 424/56 |
| 4,428,930 | 1/1984 | Chang | 424/52 |
| 4,542.167 | 9/1985 | Aoki | 523/109 |
| 4,627,977 | 12/1986 | Gaffar et al. | 424/52 |
| 4,661,341 | 4/1987 | Benedict et al. | 424/48 |
| 4,663,385 | 5/1987 | Chang et al. | 524/523 |
| 4,759,925 | 7/1988 | Gaffar et al. | 424/52 |
| 4,775,525 | 10/1988 | Pera | 424/58 |
| 4,816,245 | 3/1989 | Gaffar | 424/57 |
| 4,842,847 | 6/1989 | Amjad | 424/52 |
| 4,847,070 | 7/1989 | Pyrz et al. | 424/52 |
| 4,855,128 | 8/1989 | Lynch et al. | 424/49 |
| 4,877,603 | 10/1989 | Degenhardt et al. | 424/57 |
| 5,093,170 | 3/1992 | Degenhardt et al. | 424/52 |

FOREIGN PATENT DOCUMENTS

| | | | |
|---|---|---|---|
| 0241179 | 10/1987 | European Pat. Off. | |
| 60-142923A | 7/1985 | Japan . | |
| WO86/02831 | 5/1986 | PCT Int'l Appl. . | |
| 2151478A | 7/1985 | United Kingdom . | |

OTHER PUBLICATIONS

"Report on the Use of Triclosan/Copolymer Dentrifices in the Control of Plaque and Gingivitis," Am. J. Dent. 2: 181–240, 1989.

*Primary Examiner*—Shep K. Rose

*Attorney, Agent, or Firm*—Katherine L. Stewart; Jerry J. Yetter; Rose Ann Dabek

[57] ABSTRACT

The present invention relates to compositions and methods for inhibiting plaque. In particular, this invention relates to oral compositions comprising: (a) a safe and effective amount of a carboxy-containing copolymer having the formula $$-\!\!\left(CH_2\underset{\displaystyle COOH}{\underset{|}{C}H}\right)_{\!n}\!\!-\!\!\left(CH_2-\overset{\displaystyle COOH}{\overset{|}{\underset{\underset{\displaystyle COOH}{\underset{|}{(CH_2)_p}}}{\underset{|}{C}}}}\right)_{\!m}\!\!-$$

or the salts thereof, wherein n is in the range of from about 200 to about 14,000, m is in the range of from about 2 to about 5,000, and p is in the range of from 1 to 3; and (b) a pharmaceutically acceptable carrier. These compositions inhibit plaque without staining the teeth which are contacted with the composition.

This invention also relates to a method of inhibiting plaque on tooth surfaces in the oral cavity. This method involves applying a safe and effective amount of the carboxy-containing copolymer active agent to the oral cavity. Such an application is typically made by applying the above-described oral compositions containing the carboxy-containing copolymer to the oral cavity. The application does not stain the teeth on which it is made.

14 Claims, No Drawings

USE OF A CARBOXY-CONTAINING COPOLYMER TO INHIBIT PLAQUE FORMATION WITHOUT TOOTH STAINING

This is a continuation of application Ser. No. 07/561,832, filed on Aug. 2, 1990, now abandoned.

TECHNICAL FIELD

The present invention relates to a method of inhibiting plaque formation on teeth. In particular, it relates to a method of inhibiting plaque formation on teeth wherein the tooth surface is coated with a carboxy-containing copolymer active agent. This invention also relates to oral compositions containing said active agent and a pharmaceutically acceptable carrier.

BACKGROUND OF THE INVENTION

Dental plaque is a combination of minerals and bacteria. The bacteria associated with plaque can cause inflammatory gingivitis. Gingivitis, in turn, may lead to periodontitis. Therefore, it would be highly desirable to develop compositions and methods for inhibiting plaque. As such, numerous compositions and methods for inhibiting the formation of plaque are reported in the literature.

U.S. Pat. No. 4,847,070, issued Jul. 11, 1989, to Pyrz et al., discloses oral compositions which are effective against calculus and contain a chelating agent which is an acrylic acid polymer or copolymer or EDTA, a strontium ion source, a fluoride ion source, a pyrophosphate ion source, and a pharmaceutically acceptable carrier. The mass average molecular weight of the acrylic acid polymer or copolymer used in this invention may be in the range of about 1,000 to about 1,200,000.

U.S. Pat. No. 4,816,245, issued Mar. 28, 1989, to Gaffar, discloses a method of inhibiting human dental plaque and gingivitis involving regular application to the oral cavity of an oral composition containing an effective plaque- and gingivitis-inhibiting amount of polyvinyl phosphonic acid, or salt thereof, having a number average molecular weight of about 4,000 to 9,100.

U.S. Pat. No. 4,775,525, issued Oct. 4, 1988, to Pera, discloses a dental treatment composition and method for reducing dental plaque. The disclosed method comprises treating dental surfaces with a composition containing sodium alginate, which acts as a calcium ion chelating agent which weakens the bond between the plaque and the teeth, thereby allowing easy removal of the plaque by subsequent brushing. The compositions disclosed in this patent may also contain benzalkonium chloride and zinc sulfate, which provide for desensitizing the teeth and eliminating of halitosis.

U.S. Pat. No. 4,759,925, issued Jul. 26, 1988, to Gaffar et al., discloses the use of a mixture of the perfluoroalkyl surfactant of the general formula $C_xF_{2x+1}(CH_2)_nS(CH_2)_{n'}CO_2M$, wherein x is an integer of 3–8, n and n' are independently integers of 2 to 4, and M is hydrogen, and an alkali metal or ammonium as a dentifrice or a mouthwash with the benefit of preventing plaque formation.

U.S. Pat. No. 4,627,977, issued Dec. 9, 1986, to Gaffar et al., discloses an oral composition containing a calculus-inhibiting amount of a linear molecularly dehydrated polyphosphate salt and, to inhibit enzymatic hydrolysis of said polyphosphate salt in saliva, a combination of a fluoride ion-providing source and a synthetic anionic linear polymeric polycarboxylate.

U.S. Pat. No. 4,528,179, issued Jul. 9, 1985, to Gaffar, discloses a method of inhibiting human dental plaque and gingivitis by the regular application to the oral cavity of an oral composition containing an effective plaque- and gingivitis-inhibiting amount of polyvinyl phosphonic acid or salt thereof. The polyvinyl phosphonic acid of this reference has a preferred number average molecular weight of about 6,000 to about 100,000.

U.S. Pat. No. 4,428,930, issued Jan. 31, 1984, to Chang, discloses a dentifrice composition containing a water-dispersible, membrane-forming material which, when applied to tooth surfaces in an oral environment, attaches thereto and forms a substantially continuous hydrophobic barrier thereon, which hydrophobic barrier substantially reduces elution of a previously applied therapeutic agent. This patent also discloses a method for inhibiting plaque formation on teeth which comprises contacting the teeth with an effective amount of the above-described composition. Polymeric anionic membrane forming materials disclosed as useful in the compositions of this patent include a class of polymers having a polyolefinic main chain with acid functionalities pendent therefrom. Typical of the materials which can comprise the polyolefinic main chain are polymers of ethylene, propylene, styrene, unsaturated carboxylic acids, and copolymers of two or more of these materials. Representative polymeric anionic membrane forming materials disclosed as useful in the compositions of this patent include polyacrylic acid having a molecular weight in the range of 2,000 to 4,000,000; sodium polystyrenesulfonate having a molecular weight in the range of about 5,000 to 6,000,000; "Gantrez AN", available from GAF corporation; polyvinyl phosphate; and copolymers of acrylates which contain pendent carboxyl groups.

U.S. Pat. No. 4,375,461, issued Mar. 1, 1983, to Gander et al., discloses compositions and methods for preventing the attachment of dental plaque to the surfaces of the teeth of mammals. These disclosed compositions and methods comprise certain sulfonated vinylaromatic homopolymers and copolymers and the pharmaceutically acceptable salts thereof in a pharmaceutically acceptable vehicle, and a periodic application thereof to teeth. Hydrophilic polymeric anionic sulfates useful for dental plaque control in accordance with the disclosure of this patent are essentially sulfonated homopolymers of both unsubstituted and substituted styrene, 1-vinylnaphthalene, 2-vinylnaphthalene, and acenaphthylene, and certain copolymers thereof. Representative examples of vinyl aromatic monomers, homopolymers, and copolymers which are available in commerce and can be converted to the hydrophilic polymeric sulfonates of this patent are the following: (a) polystyrene and sodium polystyrene sulfonate of varying molecular weights available from Pressure Chemical Company; (b) styrene/butadiene (85/15) copolymer; (c) styrene/isobutylene (60/40) copolymer; (d) vinylbenzyl chloride monomer, 60/40 meta-/paraisomers, available from Dow Chemical Company; and (e) halostyrene monomers available from Polysciences Inc., and Aldrich Chemical Company.

U.S. Pat. No. 4,362,713, issued Dec. 7, 1982, to Buck, discloses compositions and methods for preventing the attachment of dental plaque to the teeth of mammals. The disclosed compositions and methods comprise certain salts of certain maleic acid copolymers in a pharmaceutically acceptable vehicle and the periodic application thereof to teeth. This patent further discloses that certain hydrophilic alkali metal and ammonium salts of 1:1 copolymers of styrene and maleic acid and 1:1 copolymers of certain linear 1-alkenes and maleic acid have been found to inhibit the deposition of dental plaque onto human teeth when applied thereon.

U.S Patent 4,224,309, issued Sep. 23, 1980, to Gaffar et al., discloses an oral composition containing an antibacterial antiplaque agent and an anti-stain additive which reduces staining caused by the antibacterial antiplaque agent, without substantially diminishing the activity of the antibacterial antiplaque agent. Bis-biguanido hexanes, such as chlorhexidine and alexidine, and quaternary ammonium salts, such as benzethonium chloride and cetyl pyridinium chloride, are typical examples of antibacterial agents. The anti-stain additive is 2-phosphono-butane-1,2,4-tricarboxylic acid or an orally acceptable salt thereof.

U.S. Pat. No. 4,138,477, issued Feb. 6, 1979, to Gaffar, discloses a composition which is useful for the prevention and control of mouth odor and is also effective in preventing calculus, plaque, caries and periodontal disease. This composition contains, as its essential agent, a zinc-polymer combination formed by the reaction or interaction of a zinc compound with an anionic polymer containing carboxylic, sulfonic and/or phosphonic acid radicals.

U.S. Pat. No. 4,118,474, issued Oct. 3, 1978, to Gaffar et al., discloses an antibacterial oral composition effective to promote oral hygiene which contains an antibacterial antiplaque agent and an additive for reducing staining of dental surfaces without substantially diminishing the activity of the antibacterial and antiplaque agent. Bis-biguanido hexanes, such as chlorhexidine and alexidine, and quaternary ammonium salts, such as benzethonium chloride and cetyl pyridinium chloride, are typical examples of antibacterial antiplaque agents. The antistain additive is phosphonoacetic acid or salts thereof.

U.S. Pat. No. 4,118,473, issued Oct. 3, 1978, to Gaffar et al., discloses an antibacterial oral composition effective to promote oral hygiene which contains an antibacterial antiplaque agent and an additive for reducing staining of dental surfaces without substantially diminishing the activity of the antibacterial and antiplaque agent. Bis-biguanido hexanes, such as chlorhexidine and alexidine, and quaternary ammonium salts, such as benzethonium chloride and cetyl pyridinium chloride, are typical examples of antibacterial antiplaque agents. The antistain additive is an N-methylene phosphonate compound, such as iminodiacetic N-methylene phosphonic acid and salts thereof.

United Kingdom Patent Application 2151478-A, published Jul. 24, 1985, assigned to the Colgate-Palmolive Company, discloses that dental plaque and gingivitis are inhibited by the regular application to the oral cavity of an oral composition containing an effective plaque- and gingivitis-inhibiting amount of polyvinyl phosphonic acid or a salt thereof. The polyvinyl phosphonic acid, and salt thereof, have a preferred number average molecular weight of from about 6,000 to 100,000.

In spite of the many disclosures of agents useful for inhibiting and reducing plaque, the need for improved antiplaque products still exists, particularly for antiplaque products that do not cause staining of the teeth.

It is therefore an object of the present invention to provide a method for inhibiting plaque formation on teeth, without tooth staining, by applying a plaque-inhibiting, carboxy-containing copolymer active agent to the oral cavity.

It is another object of the present invention to provide for oral compositions containing such active agent copolymer and a pharmaceutically acceptable carrier.

These objects will be realized by the present invention.

SUMMARY OF THE INVENTION

The present invention embraces oral compositions comprising: (a) a safe and effective amount of a carboxy-containing copolymer active agent having the formula

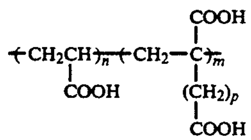

or the salts thereof, wherein n is in the range of from about 200 to about 14,000, m is in the range of from about 2 to about 5,000, and p is in the range of from 1 to 3; and (b) a pharmaceutically acceptable carrier.

The present invention also encompasses a method for inhibiting plaque formation on tooth surfaces.

DETAILED DESCRIPTION OF THE INVENTION

The oral compositions of the present invention are useful for inhibiting plaque and comprise: (a) a safe and effective amount of a carboxy-containing copolymer active agent; and (b) a pharmaceutically acceptable carrier. The compositions of this invention may optionally contain additional ingredients which include, but are not limited to, a fluoride ion source, flavoring agents, sweetening agents, and emulsifying agents.

"Oral compositions", as used herein, means a product which in the ordinary course of usage is retained in the oral cavity for a time sufficient to contact substantially all the dental surfaces and/or oral tissues for purposes of oral activity.

"Safe and effective amount", as used herein for the oral compositions of the present invention, means a sufficient amount of the carboxy-containing copolymer and other ingredients contained in such compositions for inhibiting the formation of plaque on tooth surfaces while being safe to the hard and soft tissues of the oral cavity. When used in the context of a method of applying the carboxy-containing copolymer of the present invention to the oral cavity for the purpose of inhibiting plaque formation, "safe and effective amount" means applying a sufficient amount of such carboxy-containing copolymer to the oral cavity, in unit dosage form, to inhibit the formation of plaque on tooth surfaces within the oral cavity, while being safe to the hard and soft tissues of the oral cavity.

The term "pharmaceutically acceptable carrier", as used herein, means a suitable vehicle which is pharmaceutically acceptable for application inside the oral cavity and can be used to apply the present compositions in the oral cavity.

Carboxy-Containing Copolymer Active Agent

The carboxy-containing copolymer useful as the plaque-inhibiting active agent in the oral compositions of the present invention is of the formula:

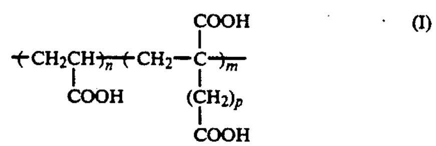

or the salts thereof, wherein n is in the range of from about 200 to about 14,000, preferably from about 2,000 to about 14,000, most preferably from about 4,000 to about 14,000, m is in the range of from about 2 to about 5,000, preferably from about 2 to about 3,000, most preferably from about 2 to about 2,000, and p is in the range of from 1 to 3, preferably from 1 to 2, most preferably 1. The copolymer active agent of the present invention preferably comprises from about 50 mole percent to about 99 mole percent, more preferably from about 70 mole percent to about 99 mole percent, most preferably from about 90 mole percent to about 99 mole percent of the acrylic acid group having the n subscript, and preferably from about 1 mole percent to about 50 mole percent, more preferably from about 1 mole percent to about 30 mole percent, most preferably from about 1 mole percent to about 10 mole percent of the structural group having the m subscript.

Based upon the range of values that the n and m subscripts may have, the mass average molecular weight of the carboxy-containing copolymer of the present invention may be in the range of from about 14,660 to about 1,798,000. However, the mass average molecular weight is typically in the range of from about 50,000 to about 1,000,000, preferably from about 200,000 to about 1,000,000, most preferably from about 400,000 to about 1,000,000.

The carboxy-containing copolymers of the present invention may be prepared by conventional, art-known techniques useful for copolymerizing acrylic acid and itaconic acid, allowing for the structural variations between itaconic acid and the structure having the m subscript. Typically, mild aqueous conditions using a conventional water-soluble free-radical initiator are used. Suitable initiators are illustrated by the common azo initiators such as 2,2'-azobis(2-amidinopropane) dihydrochloride, as well as potassium persulfate, hydrogen peroxide or the like.

A preferred carboxy-containing copolymer useful in the present invention is of the general formula:

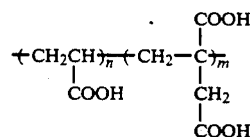

or the salts thereof, wherein n is in the range of from about 5,000 to about 14,000, and m is in the range of from about 2 to about 2,000, provided that the acrylic acid group having the n subscript comprises from about 90 mole percent to about 99 mole percent of the copolymer and the structural group having the m subscript comprises from about 1 mole percent to about 10 mole percent of the copolymer. This preferred carboxy-containing copolymer may be prepared by the method described in Example I of this document.

The carboxy-containing copolymer of the present invention may comprise repeating units of the two-monomer block shown as structure I, it may comprise a block polymer, such as when a long chain of the monomer containing the n subscript is joined with a long chain of the monomer containing the m subscript, or it may comprise a random mixture of the individual monomers of the two-monomer block shown as structure I.

Mixtures of carboxy-containing copolymers of the general formula of structure I may be used as the plaque-inhibiting active agent in the compositions of the present invention. For example, polymers having differing molecular weights or polymers having a differing order of individual monomers may be mixed together. The mass average molecular weight of active agent in such polymer mixture typically ranges from about 50,000 to about 1,000,000, preferably from about 200,000 to about 1,000,000, most preferably from about 400,000 to about 1,000,000. Mixtures of high molecular weight and low molecular weight carboxy-containing copolymers may be used to achieve a polymer mixture having an appropriate mass average molecular weight.

The salts of the carboxy-containing copolymer of the present invention are prepared by neutralizing one or more of the available carboxylic acid groups of the carboxy-containing copolymer with a cation. While not required, it is preferred that such salts be water-soluble. Examples of cations useful in the present invention include, but are not limited to, alkali metal or quaternary ammonium cations, with alkali metals being preferred, and sodium being most preferred.

The carboxy-containing copolymer useful in the present invention may optionally be interspersed with other monomers. Preferred are monomers which add carboxylate groups to the polymer.

The compositions of the present invention comprise a safe and effective amount of the carboxy-containing copolymer active agent (a) along with the pharmaceutically acceptable carrier (b). Such compositions typically comprise from about 0.10% to about 10.0% by weight, preferably from about 1.0% to about 10.0% by weight, most preferably from about 1.0% to about 6.0% by weight of the carboxy-containing copolymer (a), and from about 99.9% to about 90.0% by weight, preferably from about 99.0% to about 90.0% by weight, most preferably from about 99.0% to about 94.0% by weight of the pharmaceutically acceptable carrier (b). In particular, for both dentifrice and mouthwash compositions, the most preferred concentration of active agent ranges from about 1.0% to about 6.0% by weight.

As discussed above, the carboxy-containing copolymer of the present invention is useful for inhibiting the formation of plaque on the tooth surface. While not intending to necessarily be limited thereby, it is believed that this plaque-inhibiting carboxy-containing copolymer active agent is additionally beneficial in that it inhibits plaque formation without discernibly staining the surface of the treated teeth.

Pharmaceutically Acceptable Carrier

The carrier for the plaque-inhibiting active agent of the present invention can be any vehicle suitable for use in the oral cavity, including the usual components of mouthwashes, toothpastes, topical dental gels, toothpowders, prophylaxis pastes, lozenges, gums and the like, and are more fully described hereinafter. Without necessarily being limited thereby, the compositions of the present invention are typically prepared for rinsing and purging from the oral cavity, not for substantial oral ingestion. Dentifrices and mouthwashes are the preferred systems, with toothpastes being the more preferred.

Toothpastes and toothpowders contain as a major component an abrasive. The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al., in U.S. Pat. No. 3,070,510, issued Dec. 25, 1962, which is incorporated herein by reference. Mixtures of abrasives may also be used.

Various types of silica dental abrasives can provide the unique benefits of exceptional dental cleaning and polishing performance without unduly abrading tooth enamel or dentin. Silica abrasive materials are also exceptionally compatible with sources of soluble fluoride and other ion sources. For these reasons they are preferred for use herein. Of course the abrasive selected should also exhibit excellent compatibility with soluble strontium ion sources.

The silica abrasive polishing materials useful herein, as well as the other abrasives, generally have an average particle size ranging between about 0.1 and 30 microns, preferably between 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, issued Jun. 21, 1975, both of which are incorporated herein by reference. Preferred are the silica xerogels marketed under the tradename "Syloid" by the W. R. Grace & Company, Davidson Chemical Division. Preferred precipitated silica materials include those marketed by the J. M. Humber Corporation under the tradename "Zeodent", particularly the silica carrying the designation "Zeodent 119". These silica abrasives are described in U.S. Pat. No. 4,340,583, issued Jul. 29, 1982, the disclosure of which is incorporated herein by reference.

The abrasive in the dentifrice compositions described herein is present at a level of from about 6% to about 70%, preferably from about 15% to about 25% when the dentifrice is a toothpaste. Higher levels, as high as 90%, may be used if the composition is a toothpowder.

Another embodiment of the prevent invention is a mouthwash composition. Conventional components of mouthwash compositions include the carrier for the active agent of the present invention. Typical carriers include water and water/ethanol mixtures, with the water/ethanol mixtures being preferred. The ethanol is preferably included in the composition of the present invention due to its properties as a preservative and a solubilizing agent. Mouthwashes generally comprise from about 20:1 to about 2:1 of a water/ethanol mixture and preferably other ingredients such as flavoring agents, sweeteners, humectants and sudsing agents such as those described above. In a preferred embodiment, the mouthwash composition will contain one or more humectants, such as glycerin and sorbitol, to give a moist feel to the mouth. Generally, on a weight basis the mouthwashes of the present invention comprise from about 5% to about 60%, preferably from about 10% to about 25%, of ethanol; from 0% to about 20%, preferably from about 5% to about 20%, of a humectant; from 0% to about 2%, preferably from about 0.01% to about 0.15%, of an emulsifying agent; from 0% to about 0.5%, preferably from about 0.005% to about 0.06%, of a sweetening agent such as saccharin; from 0% to about 0.3%, preferably from about 0.03% to about 0.3%, of a flavoring agent; and the balance water.

Suitable lozenge and chewing gum components are disclosed in U.S. Pat. No. 4,083,955, issued Apr. 11, 1978 to Grabenstetter et al., which is incorporated herein by reference.

Suitable topical dental gels generally comprise a base of a humectant such as glycerin thickened with a suitable agent. Such gels generally do not contain an abrasive.

The plaque-inhibiting active agents of the present invention have been shown to be highly effective in reducing the deposition of plaque on the tooth surface in in vitro testing.

The in vitro test procedure employed in ascertaining the plaque-inhibiting properties of said active agents is carried out follows: 25 mgs. of hydroxyapatite (HAP) beads are precoated with human saliva for 1.5 hours. The HAP beads are then washed three times with a buffer solution of 0.05M KCl, 1 mM $PO_4$ (pH 6.0), 1 mM $CaCl_2$ and 0.1 mM $MgCl_2$. The HAP beads are then equilibrated with an aqueous solution of the carboxy-containing copolymer of the formula disclosed herein (at a desired concentration such as 5%), at pH 7.0, for 5 minutes with agitation. The HAP beads are removed from the aqueous solution and then washed once with a buffer solution as described above.

For the bacteria adsorption studies, 25 mg of the HAP beads prepared as described above are placed in 1.0 ml of a cell suspension comprising about $1.5 \times 10^8$ $^3H$ radiolabelled bacteria (*S. sanguis*) in a buffer solution as described above. The beads are equilibrated in the mixture for three hours, with agitation. The beads are allowed to settle for one minute and the supernatant, which contains unadsorbed cells, is removed. The HAP beads are washed three times with buffer solution (same composition as described above), collected by filtration, and dissolved in hydrochloric acid. Radioactivity of the dissolved HAP is then measured by liquid scintillation counts in order to determine the number of bound cells. These results are compared to the radioactivity of dissolved HAP that was prepared as a control without antiplaque agents.

OPTIONAL INGREDIENTS FOR USE IN ORAL COMPOSITIONS

In addition to the above-described components, the oral compositions of the present invention may include a number of optional ingredients.

Such optional ingredients include a safe and effective amount of a fluoride ion source, which typically is in the form of a water-soluble fluoride compound. This water-soluble fluoride compound is typically present in the compositions of this invention in an amount sufficient to give a fluoride concentration of from about 0.0025% to about 5.0% by weight, preferably from about 0.005% to about 2.0% by weight. Preferred fluorides are sodium fluoride, stannous fluoride, indium fluoride, acidulated phosphate fluoride and sodium monofluorophosphate. U.S. Pat. No. 2,946,735, issued Jul. 26, 1960 to Norris et al., and U.S. Pat. No. 3,678,154, issued Jul. 18, 1972 to Widder et al., disclose such salts as well as others. The disclosures of these patents are incorporated herein by reference.

Flavoring agents can also be added to the dentifrice and other compositions of the present invention. Suitable flavoring agents include oil of wintergreen, oil of peppermint, oil of spearmint, oil of sassafras and oil of clove. Sweetening agents are also useful and include aspartame, acesulfame, saccharin, dextrose, levulose and sodium cyclamate. Flavoring and sweetening agents are generally used in the compositions herein at levels of from about 0.005% to about 2% by weight.

The compositions of this invention may also contain emulsifying agents. Suitable emulsifying agents are those which are reasonably stable and foam throughout a wide pH range, and include non-soap anionic, nonionic, cationic, zwitterionic and amphoteric organic synthetic detergents. Many of these suitable surfactants are disclosed by Gieske et al. in U.S. Pat. No. 4,051,234, issued Sep. 27, 1977, which is incorporated herein by reference.

Water may also be present in the compositions of this invention. Water employed in the preparation of commercially suitable compositions should preferably be deionized and free of organic impurities. Water generally comprises from about 10% to about 50% by weight, preferably from about 20% to about 40% by weight, of the toothpaste compositions herein. These amounts of water include the free water which is added plus that which is introduced with other materials, such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic and gum tragacanth, and polysaccharide gums such as xanthan gum can also be used. Colloidal magnesium aluminum silicate or finely divided silica can be used as part of the thickening agent to further improve texture. Thickening agents in an amount from about 0.5% to about 5.0% by weight of the total composition may be used.

It is also desirable to include a humectant in a toothpaste to keep it from hardening. Suitable humectants include glycerin, sorbitol and other edible polyhydric alcohols at a level of from about 10% to about 70% by weight.

The pH of the present compositions and/or its pH in the mouth can be any pH which is safe for the mouth's hard and soft tissues. Such pH's are generally from about 3 to about 10, preferably from about 4 to about 9.

In addition to the above-described oral compositions, the present invention also encompasses a method of inhibiting plaque formation on tooth surfaces in the oral cavity. This method involves applying a safe and effective amount of the carboxy-containing copolymer of the present invention, in unit dosage form, to the oral cavity. Generally, in such an application from about 0.0015 grams to about 0.15 grams, preferably from about 0.015 grams to about 0.15 grams, most preferably from about 0.015 grams to about 0.075 grams of the carboxy-containing copolymer of the present invention is applied to the oral cavity. Such application of the carboxy-containing copolymer of the present invention is typically made by applying the oral compositions of the present invention containing the carboxy-containing copolymer to the oral cavity. When the oral composition is a toothpaste, typically from about 0.50 grams to about 2.5 grams, preferably from about 0.50 grams to about 2.0 grams, most preferably from about 1.0 grams to about 2.0 grams of toothpaste containing from about 0.10% to about 10.0% by weight, preferably from about 1.0% to about 10.0% by weight, most preferably from about 1.0% to about 6.0% by weight of the carboxy-containing copolymer of the present invention is applied to an applicating device, e.g., a toothbrush. The applicating device is then contacted with the tooth surface in a manner such that the toothpaste is contacted with the tooth surface. The applicating device may be further used to obtain an improved distribution of the toothpaste, and consequently the carboxy-containing copolymer, onto the tooth surface, for example by brushing. The brushing will typically last for a period of 2 minutes, although the actual time period of brushing is dependent upon the individual user. Following brushing, the toothpaste residue is typically removed from the tooth surface by using a liquid acceptable to the oral cavity, typically water, to rinse the oral cavity. Typically 10 ml. of water will suffice for such rinsing. Following rinsing, the liquid is typically expectorated from the oral cavity.

When the oral composition is embodied in a mouthwash, typically from about 5.0 to about 20.0 ml., preferably from about 5.0 to about 15.0 ml., most preferably about 10 ml. of liquid mouthwash containing from about 0.10% to about 10.0% by weight, preferably from about 1.0% to about 10.0% by weight, most preferably from about 1.0% to about 6.0% by weight of the carboxy-containing copolymer of the present invention is introduced to the oral cavity. The liquid mouthwash is then agitated, preferably for a period of 2 minutes, within the oral cavity to obtain an improved distribution of the mouthwash, and consequently the carboxy-containing copolymer, onto the tooth surface. The actual time of agitation is dependent upon the individual user. Following agitation, the mouthwash is typically expectorated from the oral cavity.

EXAMPLES

The following are representative oral compositions of the present invention.

EXAMPLE I

A poly(acrylic acid-itaconic acid) copolymer useful in the present invention may be prepared as follows:

Starting-materials

Acrylic acid (Polysciences Inc., Warrington, PA.) is vacuum distilled through a Vigreux column and is preferably used fresh in subsequent operations, e.g., within one day of distillation. Itaconic acid (Aldrich Chemical Co., Milwaukee, WI.) is obtained in 99% +purity and is used as received. The free-radical initiator 2,2'-azobis(2-amidinopropane) dihydrochloride (WAKO V-50, Wako Pure Chemical Industries, Osaka, Japan) is also used as received. Unless otherwise noted, water is triply distilled. Where polymers are dialyzed, the dialysis membrane is obtained from Spectrum Medical Industries, Inc., Los Angeles, Calif.

Preparation of the poly(acrylic acid-itaconic acid) copolymer (90 mole % acrylic acid group, 10 mole % itaconic acid group)

Acrylic acid (25.000 g, 0.34693 mole), itaconic acid (5.0151 g, 0.038548 mole), Wako V-50 (0.1046 g, 0.3856 millimole), and 193 ml of water, which has been acidified to pH 2.0 with hydrochloric acid, are added to a 500 ml three-necked round-bottomed flask. The necks are fitted with a thermometer, a stopper, and a gas inlet/outlet adapter capable of bubbling gas through a liquid in the flask and venting it. The solution is deaerated by passage of nitrogen gas and is then placed under an atmosphere of argon. The solution is heated to 60° C. and is maintained at this temperature for 15 hours. The viscous solution of copolymer is cooled to ambient temperature and is dialzyed against distilled water overnight (Spectrapor 3 tubing with molecular weight cut-off at 3500) to remove any unreacted monomers. The dialyzed solution is freeze dried to give 28.31 g of poly(acrylic acid-itaconic acid) copolymer as a colorless solid. The mass average molecular weight, as determined by low angle laser light scattering in 0.2 Molar sodium chloride in water (refractive index=1.3344, $d_n/d_c$=0.1683), is 658,200.

EXAMPLE II

Preparation of another poly(acrylic acid-itaconic acid) copolymer suitable for use in the present invention (90 mole % acrylic acid group, 10 mole % itaconic acid group).

Acrylic acid (20.000 g, 0.27755 mole), itaconic acid (4.0121 g, 0.038386 mole), Wako V-50 (0.0837 g, 0.308 millimole), and 150 ml of water, which has been acidified to pH 2.0 with hydrochloric acid are added to a 250 ml three-necked round-bottomed flask. The necks are fitted with a thermometer, a stopper, and a gas inlet/-outlet adapter capable of bubbling gas through a liquid in the flask and venting it. The solution is deaerated by passage of nitrogen gas and is then placed under an atmosphere of argon. The solution is heated to 55° C. and is maintained at this temperature for 15 hours. The viscous solution of copolymer is cooled to ambient temperature and is dialyzed against distilled water overnight (Spectrapor 3 tubing with molecular weight cut-off at 3500) to remove any unreacted monomers. The dialyzed solution is freeze dried to give 23.00 g of poly(acrylic acid-itaconic acid) copolymer as a colorless solid. The mass average molecular weight, as determined by low angle laser light scattering in 0.2 Molar sodium chloride in water (refractive index=1.3344, $d_n/d_c$—0.1683), is 896,100.

EXAMPLE III

Preparation of another poly(acrylic acid-itaconic acid) copolymer suitable for use in the present invention (90 mole % acrylic acid group, 10 mole % itaconic acid group).

Acrylic acid (105.27 g, 1.4609 moles), itaconic acid (21.12 g, 0.1623 mole), Wako V-50 (0.4403 g, 1.623 millimole), and 812 ml of water, which has been acidified to pH 2.0 with hydrochloric acid, are added to a 2 liter three-necked round-bottomed flask. The necks are fitted with a thermometer, a stopper, and a gas inlet/-outlet adapter capable of bubbling gas through a liquid in the flask and venting it. The solution is deaerated by passage of nitrogen gas and is then placed under an atmosphere of argon. The solution is heated to 55° C. and maintained at this temperature for 15 hours. The viscous solution of copolymer is cooled to ambient temperature and is freeze dried to give 121.57 g of poly(acrylic acid-itaconic acid) copolymer as a colorless solid. The mass average molecular weight, as determined by low angle laser light scattering on a dialyzed portion in 0.2 Molar sodium chloride in water (refractive index=1.3344, $d_n/d_c$=0.1683), is 821,600.

EXAMPLE IV

Preparation of another poly(acrylic acid-itaconic acid) copolymer suitable for use in the present invention (90 mole % acrylic acid group, 10 mole % itaconic acid group).

Acrylic acid (1050.0 g, 14.571 moles), itaconic acid (210.64 g, 1.6190 moles), Wako V-50 (4.3919 g, 16.19 millimole), and 7.9 liters of water, which has been acidified to pH 2.0 with hydrochloric acid, are added to a 22 liter three-necked round-bottomed flask fitted with a thermometer, a mechanical stirrer, and gas inlet/outlet adapter capable of bubbling gas through a liquid in the flask and venting it. The solution is deaerated by passage of nitrogen gas and is then placed under an atmosphere of nitrogen. The solution is heated to 55° C. and maintained at this temperature for 15 hours. The viscous solution of copolymer is cooled to ambient temperature and is freeze dried to give 1,222.1 g of poly(acrylic acid-itaconic acid) copolymer as a colorless solid. The mass average molecular weight, as determined by low angle laser light scattering on a dialyzed portion in 0.2 Molar sodium chloride in water (refractive index=1.3344, $d_n/d_c$—0.1683), is 711,700.

EXAMPLE V

Preparation of another poly(acrylic acid-itaconic acid) copolymer suitable for use in the present invention (95 mole % acrylic acid group, 5 mole % itaconic acid group).

Acrylic acid (25.00 g, 0.3469 mole), itaconic acid (2.376 g, 18.26 millimole), Wako V-50 (0.0991 g, 0.365 millimole), and 183 ml of water, which has been acidified to pH 2.0 with hydrochloric acid, are added to a 500 ml three-necked round-bottomed flask. The necks are fitted with a thermometer, a stopper, and a gas inlet/outlet adapter capable of bubbling gas through a liquid in the flask and venting it. The solution is deaerated by passage of nitrogen gas and is then placed under an atmosphere of argon. The solution is heated to 55° C. and maintained at this temperature for 15 hours. The viscous solution of copolymer is cooled to ambient temperature and is dialyzed against distilled water overnight (Spectrapor 3 tubing as in the foregoing Examples) to remove any unreacted monomers. The dialyzed solution is freeze dried to give 25.99 g of poly(acrylic acid-itaconic acid) copolymer as colorless solid. The mass average molecular weight, as determined by low angle laser light scattering in 0.2 Molar sodium chloride in water (refractive index=1.3344, $d_n/d_c$=0.1683), is 683,900.

EXAMPLE VI

Preparation of another poly(acrylic acid-itaconic acid) copolymer suitable for use in the present invention (95 mole % acrylic acid group, 5 mole % itaconic acid).

Acrylic acid (21.11 g, 0.2930 mole), itaconic acid (2.0061 g, 15.420 millimole), Wako V-50 (0.0837 g, 0.309 millimole), and 150 ml of water, which has been acidified to pH 2.0 with hydrochloric acid, are added to a 250 ml three-necked round-bottomed flask. The necks are fitted with a thermometer, a stopper, and a gas inlet/outlet adapter capable of bubbling gas through a liquid in the flask and venting it. The solution is deaerated by passage of nitrogen gas and is then placed under an atmosphere of argon. The solution is heated to 55° C. and maintained at this temperature for 15 hours. The viscous solution of copolymer is cooled to ambient temperature and is dialyzed against distilled water overnight (Spectrapor 3 tubing as in the foregoing Examples) to remove any unreacted monomers and then freeze dried to give 1.5 g of poly(acrylic acid-itaconic acid) copolymer as a colorless solid. The mass average molecular weight, as determined by low angle laser light scattering in 0.2 Molar sodium chloride in water (refractive index=1.3344, $d_n/d_c=0.1670$), is 925,000.

EXAMPLE VII

The following is a representative example of a toothpaste prepared with the active agent of the present invention.

| Component | Wt % |
|---|---|
| Distilled Water | 17.50 |
| Sorbitol (70% Aqueous Solution) | 49.50 |
| Sodium Saccharin | 0.30 |
| Dye Solution | 0.35 |
| Precipitated Silica | 20.00 |
| Sodium Fluoride | 0.25 |
| Flavor | 1.30 |
| Sodium Alkyl Sulfate (27.9% Aqueous Solution) | 5.00 |
| Carbopol 940S (Available from B. F. Goodrich) | 0.20 |
| Xanthan Gum | 0.60 |
| Poly(acrylic acid-itaconic acid) Copolymer of Example I | 5.00 |
| | 100.00 |

The above composition is made by combining the water and part of the sorbitol in an agitated mixture and heating this mixture to 40° F. The poly(acrylic acid-itaconic acid) copolymer, saccharin, sodium fluoride and precipitated silica are then added in order and the total mixture is mixed for a period ranging from 5 to 10 minutes. The flavor, dye and surfactant are then added. In a separate vessel the remainder of the sorbitol, the Carbopol and the xanthan gum are slurried together and then added to the main mix tank. The complete batch is mixed for about one-half hour and subsequently milled and deaerated.

EXAMPLE VIII

The following is another representative example of a toothpaste prepared using the active agent of the present invention

| Component | Wt % |
|---|---|
| Sorbitol (70% Aqueous Solution) | 50.75 |
| Distilled Water | 16.50 |
| Sodium Saccharin | 0.30 |
| Dye Solution | 0.35 |
| Precipitated Silica | 20.00 |
| Sodium Fluoride | 0.25 |
| Flavor | 1.30 |
| Sodium Alkyl Sulfate (27.9% Aqueous Solution) | 5.00 |
| Carbopol 940s | 0.20 |
| Xanthan Gum | 0.60 |
| Poly(acrylic acid - itaconic acid) Copolymer of Example III | 4.75 |
| | 100.00 |

In addition to the levels and combinations of ingredients shown in these examples, others can be used which are consistent with the invention disclosed.

EXAMPLE IX

This example shows a mouth rinse composition containing the poly(acrylic acid-itaconic acid) copolymer active agent of the present invention.

The mouth rinse is prepared as follows:

| Component | Wt % |
|---|---|
| Poly(acrylic acid-itaconic acid) Copolymer of Example I | 4.00 |
| Distilled $H_2O$ | 69.19 |
| Ethanol | 16.25 |
| Glycerin | 10.00 |
| Nonionic Surfactant | 0.12 |
| Benzoic Acid | 0.05 |
| Sodium Saccharin | 0.05 |
| Flavor | 0.15 |
| Color | 0.04 |
| NaOH (10% Sol.) | 0.15 |
| | 100.00 |

The mouth rinse is prepared by adding each of the ingredients to the distilled water and stirring.

What is claimed is:

1. An oral composition comprising: (a) a safe and effective amount of a carboxy-containing copolymer active agent having the formula

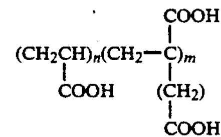

or the salts thereof, wherein n is in the range of from about 200 to about 14,000, m is in the range of from about 2 to about 5,000, the mass average molecular weight of the active agent is in the range of from about 200,000 to about 1,000,000, and the active agent comprises from about 70 mole percent to about 99 mole percent of the acrylic acid group having the n subscript and form about 1 mole percent to about 30 mole percent of the structural group having the m subscript; (b) a safe and effective amount of a fluoride ion source; and (c) a pharmaceutically acceptable dentrifice toothpaste or mouthwash carrier.

2. An oral composition according to claim 1 wherein n is in the range of from about 2,000 to about 14,000, m is in the range of from about 2 to about 3,000, and p is in the range of from 1 to 2.

3. An oral composition according to claim 2 wherein n is in the range of from about 4,000 to about 14,000, m is in the range of from about 2 to about 2,000, and p is 1.

4. An oral composition according to claim 3 wherein the mass average molecular weight of the active agent (a) is in the range of from about 400,000 to about 1,000,000.

5. An oral composition according to claim 2 which comprises from about 0.10% to about 10.0% by weight of the active agent (a).

6. an oral composition according to claim 4 which comprises from about 1.0% to about 10.0% by weight of the active agent (a).

7. An oral composition according to claim 6 which comprises from about 1.0% to about 6.0% by weight of the active agent in (a).

8. An oral composition according to claim 7 wherein the active agent (a) comprises from about 90 mole percent to about 99 mole percent of the acrylic acid group having the n subscript and from about 1 mole percent to about 10 mole percent of the structural group having the m subscript.

9. An oral composition according to claim 1 wherein the fluoride ion source is sodium fluoride present at a concentration ranging from about 0.005% to about 2.0% by weight.

10. An oral composition according to claim 1 which further comprises a silica dental abrasive.

11. A method of inhibiting plaque formation in the oral cavity comprising applying to the oral cavity a safe and effective amount, in unit dosage form, of a carboxy-containing copolymer active agent having the formula:

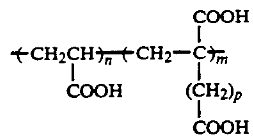

or the salts thereof, wherein n is in the range of from about 200 to about 14,000, m is in the range of from about 2 to about 5,000, and p is in the range of from 1 to 3.

12. A method according to claim 11 wherein the carboxy-containing copolymer is applied to the oral cavity in a composition in the form of a toothpaste.

13. A method according to claim 11 wherein the carboxy-containing copolymer is applied to the oral cavity in a composition in the form of a mouthwash.

14. An oral composition comprising: (a) a safe and effective amount of a poly(acrylic acid - itaconic acid) copolymer active agent having the formula

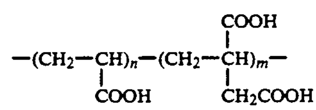

or the salts thereof, wherein n is in the range of from about 4,000 to about 14,000 and m is in the range of from about 2 to about 2,000; and (b) a pharmaceutically-acceptable carrier.

* * * * *